US010373710B2

(12) United States Patent
Valerino

(10) Patent No.: US 10,373,710 B2
(45) Date of Patent: Aug. 6, 2019

(54) SYSTEMS AND METHODS FOR PNEUMATIC TUBE DELIVERY USING SMART CARRIERS

(71) Applicant: Pevco Systems International Inc., Baltimore, MD (US)

(72) Inventor: James Valerino, Baltimore, MD (US)

(73) Assignee: Pevco Systems International Inc., Baltimore, MD (US)

( * ) Notice: Subject to any disclaimer, the term of this patent is extended or adjusted under 35 U.S.C. 154(b) by 240 days.

(21) Appl. No.: 15/191,064

(22) Filed: Jun. 23, 2016

(65) Prior Publication Data
US 2017/0372040 A1    Dec. 28, 2017

(51) Int. Cl.
*G16H 10/40* (2018.01)
*B65G 51/36* (2006.01)
*G06Q 10/08* (2012.01)
*H04W 4/80* (2018.01)
*H04W 84/18* (2009.01)
*G06Q 50/22* (2018.01)

(52) U.S. Cl.
CPC ......... *G16H 10/40* (2018.01); *G06Q 10/0833* (2013.01); *H04W 4/80* (2018.02); *B65G 51/36* (2013.01); *G06Q 50/22* (2013.01); *H04W 84/18* (2013.01)

(58) Field of Classification Search
CPC ............................................. B65G 2203/0216
USPC .............. 406/1–37, 110, 111, 147, 184–190
See application file for complete search history.

(56) References Cited

U.S. PATENT DOCUMENTS

| 6,048,086 | A  | * | 4/2000 | Valerino, Sr. ....... | B01F 11/0005 706/10 |
| 7,243,002 | B1 | * | 7/2007 | Hoganson .............. | B65G 51/44 406/4 |
| 7,500,809 | B2 | * | 3/2009 | Menday ................. | B65G 51/06 406/187 |
| 7,751,930 | B2 | * | 7/2010 | Valerino, Sr. .......... | B65G 51/06 406/2 |
| 7,950,879 | B2 | * | 5/2011 | Hoganson .............. | B65G 51/36 406/10 |
| 8,116,906 | B2 | * | 2/2012 | Valerino, Sr. .......... | G06Q 10/00 700/226 |
| 8,596,932 | B2 | * | 12/2013 | Hoganson .............. | B65G 51/36 406/12 |

(Continued)

*Primary Examiner* — William R Harp
(74) *Attorney, Agent, or Firm* — Fay Kaplun & Marcin, LLP

(57) ABSTRACT

A system for delivering items through a network of pneumatic tubing includes a network of tubing, a system controller controlling operation of the system, a plurality of carriers for delivering items. Each of the plurality of carriers includes a wireless transmission component, a plurality of workstations arranged throughout the system in communication with the network of tubing, at least one blower and at least one diverter. The at least one blower is connected to at least two workstations of the plurality of workstations via the network of tubing passing through the at least one diverter, and a plurality of system transceivers arranged throughout the network of tubing and the plurality of workstations. At least one of the system transceivers receives carrier transit information from at least one of the wireless transmission components of one of the carriers, and the system controller adjusts the operation of the system based on the carrier transit information.

20 Claims, 7 Drawing Sheets

(56) References Cited

U.S. PATENT DOCUMENTS 9,139,383 B2 * 9/2015 Hoganson .............. B65G 51/36
9,611,105 B1 * 4/2017 Powder ................. B65G 51/42
9,656,815 B2 * 5/2017 Hoganson .............. B65G 51/44

* cited by examiner

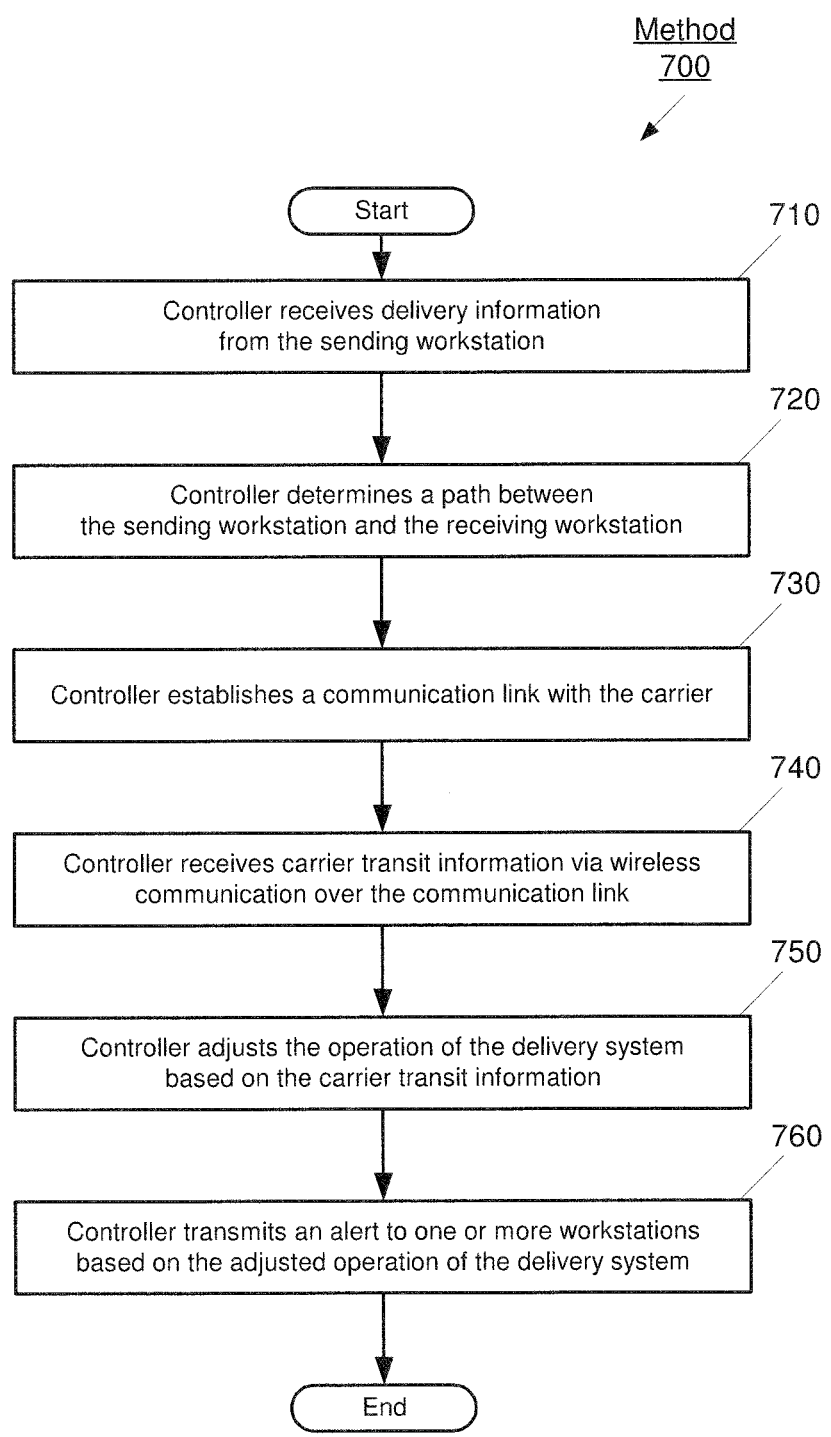

SYSTEMS AND METHODS FOR PNEUMATIC TUBE DELIVERY USING SMART CARRIERS

FIELD OF THE INVENTION

The present invention is generally directed to a pneumatic tube delivery system using smart carriers. More specifically, the subject system safely, securely, and timely transports various items through tubular conduits of a pneumatic tube delivery system while measuring variables associated with the carrier and/or the contents of the carrier and automatically taking intelligent management and control over delivery adaptively suited to transported items.

BACKGROUND

Pneumatic tube delivery systems are widely used in various institutions. Although, these systems are implemented in different forms depending on the nature of operations and transactions carried out at various facilities, the systems generally share basic components. First, a network of tubular conduits is established throughout the facility, branching to outlets connected to respective send/receive workstations, or portals. Items of interest may be transported between workstations via the conduits in capsule-like carriers, the contents of which are filled, for example, by users at sending workstations and emptied by users at receiving workstations. Alternatively, the packaging of the item itself may act as the carrier so that the item is not required to be housed within a separate carrier apparatus for delivery.

Pneumatic tube delivery systems are employed, for example, in financial institutions such as banks to remotely conduct customer transactions in real time. Industrial and retail facilities also employ these systems to transport payload items such as documents, currency, parts, or merchandise from one location to another. Perhaps the most prevalent and demanding uses are in healthcare institutions such as hospitals, where the need for quick, efficient and secure transport of physical items between remote locations within a large facility, or multiple facilities, tends to be the rule, not the exception. For instance, a pneumatic tube delivery system within the healthcare industry allows departments in hospitals to send the most delicate of items from any station to any other station in the system. Items such as pharmaceuticals, lab specimens, blood products, and the like must be passed between different staff members quickly and reliably. It is not uncommon for a hospital to carry out several thousands of transports of delicate payloads like this on a daily basis.

The carriers' travel through the network of conduits is driven by one or more blower units which generate pneumatic flow (such as by pressure or by vacuum) sufficient to propel the carriers through different portions of the network. Typically, a computer-based controller unit(s) operates to regulate carrier traffic and maintain overall system operation. The network of conduits may be quite complex even in modest sized facilities, since delivery access between every combination of workstations is often required. The network generally incorporates multi-port diverters, or transfer units, at intermediate points physically transferring carriers from one branch (or section) of the conduit network to another for delivery to the proper destination outlet. While such diverter/transfer units markedly reduce redundancy in conduit segments, the network remains quite elaborate in systems serving numerous outlets, with individual conduit segments making numerous turns and bends to serve the many workstations.

In healthcare settings, items such as blood work and other test results, may be highly time sensitive, temperature sensitive and/or impact sensitive. However, the size of certain healthcare facilities and the number of required workstations often push the limits of typical pneumatic tube delivery system. In current systems that include large numbers of workstations arranged in multiple operating subsystems, it is difficult to monitor the locations of the carriers. Furthermore it is difficult to monitor the conditions of the carriers, the contents within the carriers and the network of tubing. Hence, there is a need for a delivery routing system that permits the tracking of carriers and their contents while monitoring the status and conditions of the delivery routing system.

SUMMARY OF THE INVENTION

The present invention is directed to a pneumatic tube delivery system for transporting items via a carrier. The system comprises a network of tubing, a system controller controlling operation of the system, a plurality of carriers for delivering items, wherein each of the plurality of carriers includes a wireless transmission component, a plurality of workstations arranged throughout the system in communication with the network of tubing, at least one blower and at least one diverter, wherein the at least one blower is connected to at least two workstations of the plurality of workstations via the network of tubing passing through the at least one diverter, and a plurality of system transceivers arranged throughout the network of tubing and the plurality of workstations, wherein at least one of the system transceivers receives carrier transit information from at least one of the wireless transmission components of one of the carriers, and the system controller adjusts the operation of the system based on the carrier transit information.

The present invention is also directed to a method for transporting items via a pneumatic tube delivery system. The method includes receiving delivery information from a sending workstation of a delivery system, the delivery information including information related to a receiving workstation, determining a path from the sending work station to the receiving workstation based on the delivery information, establishing a communication link with the carrier via a wireless transmission component of the carrier while the carrier travels along the path to the receiving workstation, receiving via wireless radio communications carrier transit information pertaining to one of a delivery of the carrier along the path and a condition of the delivery system, and adjusting an operation of the delivery system based on the carrier transit information.

The present invention is also directed to a non-transitory computer readable storage medium including a set of instructions, executable by a processor, for controlling the operations of a pneumatic tube delivery system. The set of instructions, when executed by the processor, cause the processor to perform operations including receiving delivery information from a sending workstation of a delivery system, the delivery information including information related to a receiving workstation, determining a path from the sending workstation to the receiving workstation based on the delivery information, establishing a communication link with the carrier via a wireless transmission component of the carrier while the carrier travels along the path to the receiving workstation, receiving via wireless radio communications carrier transit information pertaining to one of a delivery of the carrier along the path and a condition of the delivery system, and adjusting, by a system controller, the operation of the system based on the carrier transit information.

BRIEF DESCRIPTION OF THE DRAWINGS

FIG. 7 shows an exemplary method for transporting items via a pneumatic tube delivery system according to an exemplary embodiment of the present invention.

DETAILED DESCRIPTION

Figure 1:
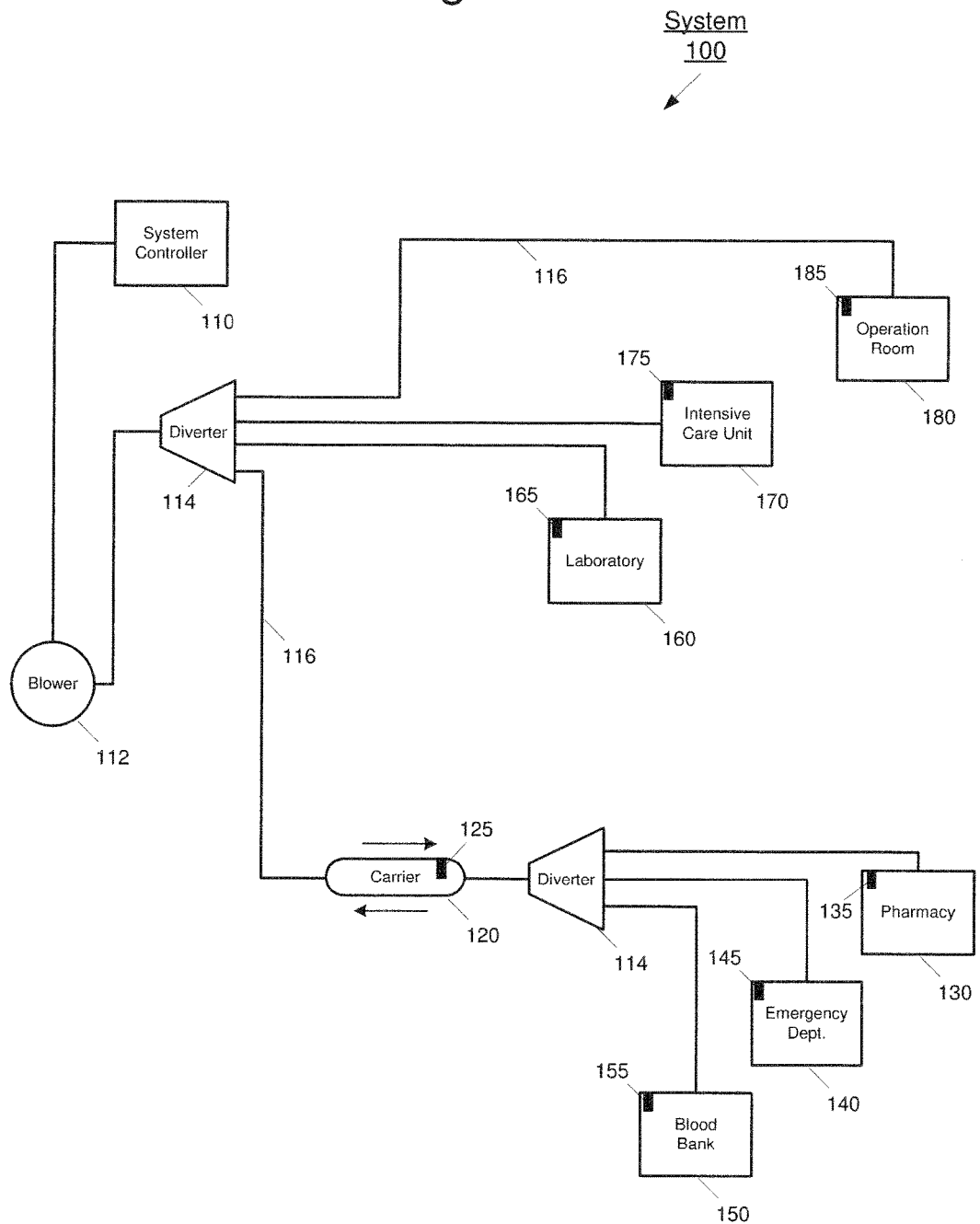
FIG. 1 shows a schematic diagram of a pneumatic tube delivery system implemented within a facility including a plurality of various departmental workstations according to an exemplary embodiment of the present invention.

The present invention may be further understood with reference to the following description and the appended drawings, wherein like elements are referred to with the same reference numerals. Exemplary embodiments describe pneumatic tube delivery systems and methods for improved performance pertaining to monitoring carriers and their contents to be transported through pneumatic conduits extending between workstations. An exemplary system and/or method may be implemented within a large facility divided into a number of departments and subsystems as desired. For instance, the large facility may be a healthcare complex composed of various departments (e.g., pharmacies, laboratories, blood banks, operating rooms, etc.), as well as separate buildings distributed across a large plot of land. According to this example, each of the buildings within the complex may define one or more subsystems. Although the exemplary embodiments describe the use of a pneumatic tube delivery system within a healthcare complex, it will be understood by those of skill in the art that the disclosed systems and methods may be used in any of a variety of locations.

As will be described in greater detail below, the exemplary systems and methods allow for a pneumatic tube delivery system to complete delivery of each carrier through the system from a sending workstation to a receiving workstation while monitoring the status of the carrier, the carrier contents, and the system during the delivery process. Sensors throughout the system and within the carrier can measure and monitor variables associated with the system and the carrier and automatically take appropriate action when predetermined conditions (e.g., thresholds) are met. The variables monitored by the sensors may include, but are not limited to, temperature, humidity, speed, force, distance traveled, time duration, system pressure, carrier inventory, sensor status (e.g., battery life, signal strength, operability, etc.). Furthermore, the placement of wireless radio communication transceivers throughout the system and/or within the carriers allow for the measurement data to be communicated between various components of the system via a wired or wireless network (e.g., a short-range, low power consumption wireless communication protocol, such as the Bluetooth standard). This provides for improved carrier tracking and content monitoring and increasing overall system efficiency and decision-making capabilities. In addition, the measurement data may interface with components of external systems, such as the management systems of the various departments (e.g., pharmacy database, laboratory database, blood bank database, etc.).

FIG. 1 shows a schematic diagram of a pneumatic tube delivery system 100 implemented within a facility including a plurality of various departmental workstations according to an exemplary embodiment of the present invention. A computer control center, or controller 110 of the exemplary pneumatic tube delivery system 100 controls the operation of the overall system 100. Furthermore, the controller 110 manages all system traffic and statistics related to the transmission of one or more carriers 120 throughout the facility. A carrier 120 is a capsule that is loaded with contents to be send from a sending workstation to a receiving workstation. According to an exemplary embodiment, the capsule 120 may include a wireless communication component 125, such as a transceiver operating according to the Bluetooth communication protocol.

The pneumatic tube delivery system 100 also includes at least one blower 112 to provide pressure and vacuum to move the carrier 120 and at least one diverter 114 to align transmission tubing 116 for a designated path from the sending workstation to the receiving workstation. Accordingly, the blower 112 and the diverter 114 are operated by the controller 110 to manage deliveries within the pneumatic tube delivery system 100 and to interface with subsystems, such as departments within the facility, for carrier deliveries. As will be described in greater detail below, any of the various system components (e.g., blowers 112, diverters 114, tubing 116, etc.) and any of the workstations of the departments may include sensors for detecting conditions within the system 100 and wireless radio transceivers for transmitting sensor measurements and information throughout the system 100.

The pneumatic tube delivery system 100 of this embodiment is deployed within a facility, such as a healthcare facility, that includes multiple departments, such as a pharmacy 130, an emergency department 140, a blood bank 150, a laboratory 160, an intensive care unit (ICU) 170 and an operating room 180. Accordingly, each of these departments may include a wireless transceiver components 135, 145, 155, 165, 175 and 185 for sending and/or receiving wireless communications with the wireless transceiver 125 of the carrier 120.

Figure 2:
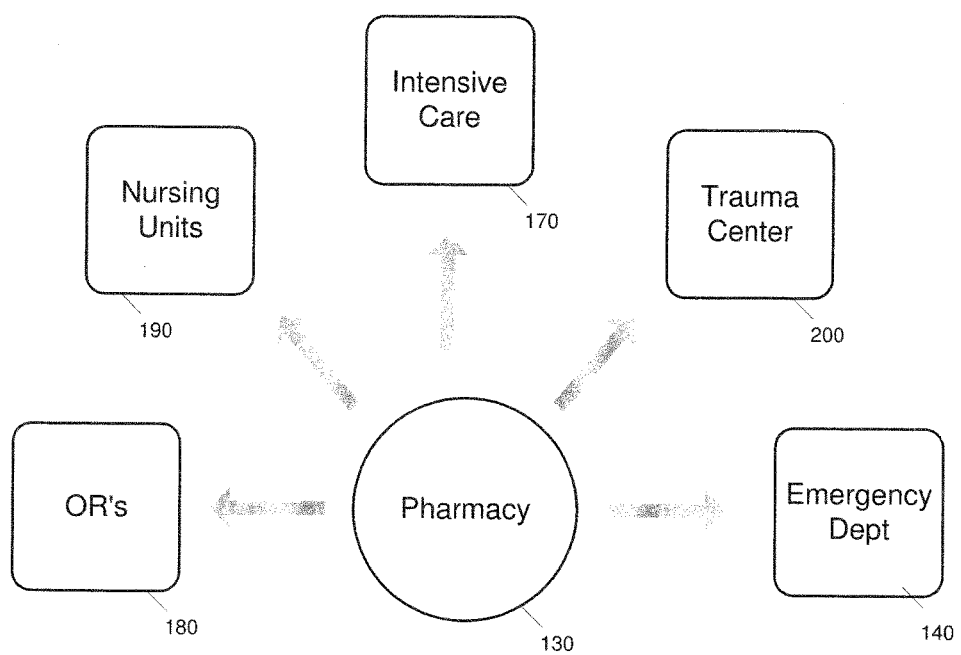
FIG. 2 shows an exemplary pharmacy sending materials to various departments within the pneumatic tube delivery system according to an exemplary embodiment of the present invention.
Figure 3:
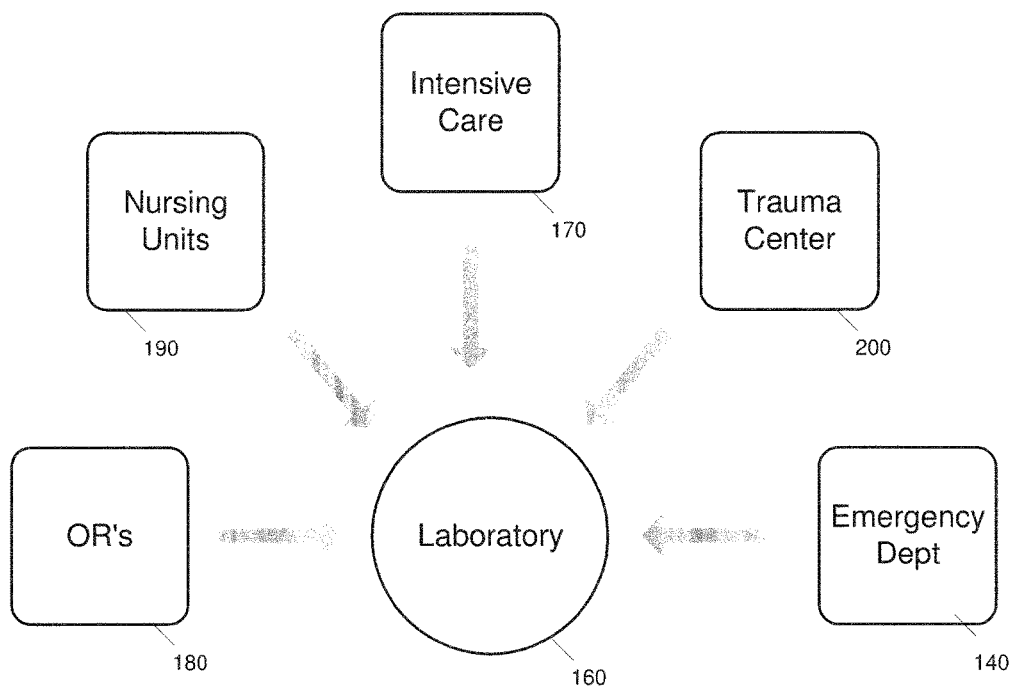
FIG. 3 shows an exemplary laboratory receiving materials from various departments within the pneumatic tube delivery system according to an exemplary embodiment of the present invention.
Figure 4:
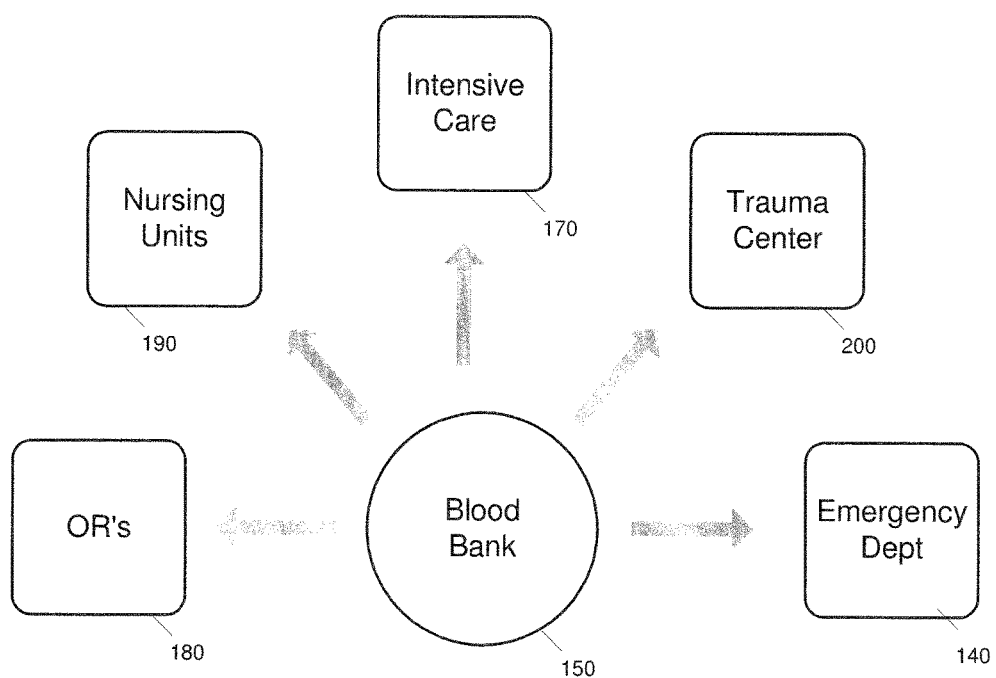
FIG. 4 shows an exemplary blood bank sending materials to various departments within the pneumatic tube delivery system according to an exemplary embodiment of the present invention.

As shown in FIG. 2, the pharmacy 130 may send materials such as narcotics, IV drips and other medication to the operating rooms 180, nursing units 190, intensive care units 170, trauma centers 200, emergency departments 140, etc. As illustrated in FIG. 3, any of the various departments (e.g., operating rooms 180, nursing units 190, intensive care units 170, trauma centers 200, emergency departments 140, etc.)

may send specimens, gross cultures and blood products to the laboratory 160. Likewise, in FIG. 4, the blood bank 150 may send blood components (e.g., PRBC, FFP), platelets, cryoprecipitates, and derivatives (e.g., Albumin) to various departments (e.g., operating rooms 180, nursing units 190, intensive care units 170, trauma centers 200, emergency departments 140, etc.). It will be understood by those of skill in the art that while the schematic diagram of FIG. 1 depicts a facility including six different departments, the exemplary system 100 may be implemented in a facility having any number of departments and delivery subsystems.

The exemplary system controller 110 receives delivery information (e.g., a receiving workstation designated to receive the carrier, carrier content information, urgency and/or handling instructions, etc.) corresponding to a carrier originating from a sending workstation of one of the departments. Based on the delivery information and current system conditions (e.g., carrier traffic, preferred routing information, staff alerts, staff access permissions and prohibitions, time of day restrictions, location restrictions, control software graphical user interface messages, error handling preferences, empty carrier handling info, out of order or other relevant status of any system components, etc.), the controller 110 creates a transportation pathway from the sending workstation to the receiving workstation. Based on this information, the controller 110 configures various components throughout the system 100, including but not limited to a selected blower 112 and one or more selected diverters 114 to create a path along the tubing 116 from the sending workstation to the receiving station. The controller 110 then operates the blower 112 to generate vacuum pressure to draw the carrier from the sending workstation to the blower 112 and then generates positive pressure to propel the carrier from the blower 112 to the receiving workstation. Those skilled in the art will understand that the exemplary embodiments may be employed with different systems in which, for example, multiple blowers are employed for a single carrier transaction in the same manner described herein.

The system controller 110 determines an appropriate transportation route, controlling blower operation and diverter configurations, based on the delivery information. The transport transaction is then carried out according to the transport characteristic settings, via, for example, a carrier apparatus through the system. In addition, where the information acquired for a payload item indicates that it is highly time-sensitive, for instance, the priority of delivery is appropriately set and the transport transaction carried out as expeditiously as priority level dictates. In addition, the transaction characteristics may indicate additional actions beyond priority level adjustment which are concurrently or collaterally effected by the system 100 as well. These actions may include, for instance, the dissemination of appropriate alerts to one or more parties and locations affected by the transport transaction. It will be understood by those of skill in the art that although the exemplary embodiments describe carriers and carrier apparatuses, the payload items are not required to be separately housed in a carrier apparatus and, in some situations, the packaging of the payload item itself, may act as the carrier.

Any and/or all of the workstations and the carriers may include wireless transmitters and an arrangement of sensors. The arrangement of sensors may read and store information associated with the carriers, the carrier contents and the system. The sensors may also read and store information associated with the sending workstation and the receiving workstation as well as any or all other components of the system. The wireless transmitters may send the information from any of the sensors to system controller 110. For instance, the wireless transmitters may utilize short-range radio communication, such as Bluetooth, to receive and transmit information. The system controller 110 receives information from one or more of the wireless transmitters (or through other network components in communication with the wireless transmitters) and determines the appropriate actions to be performed for the delivery of the carrier. For example, the system controller 110 may use the information to determine to which receiving workstation the carrier will be routed and which sensors should acknowledge the transmission of the carrier as it moves through the system.

Figure 5:
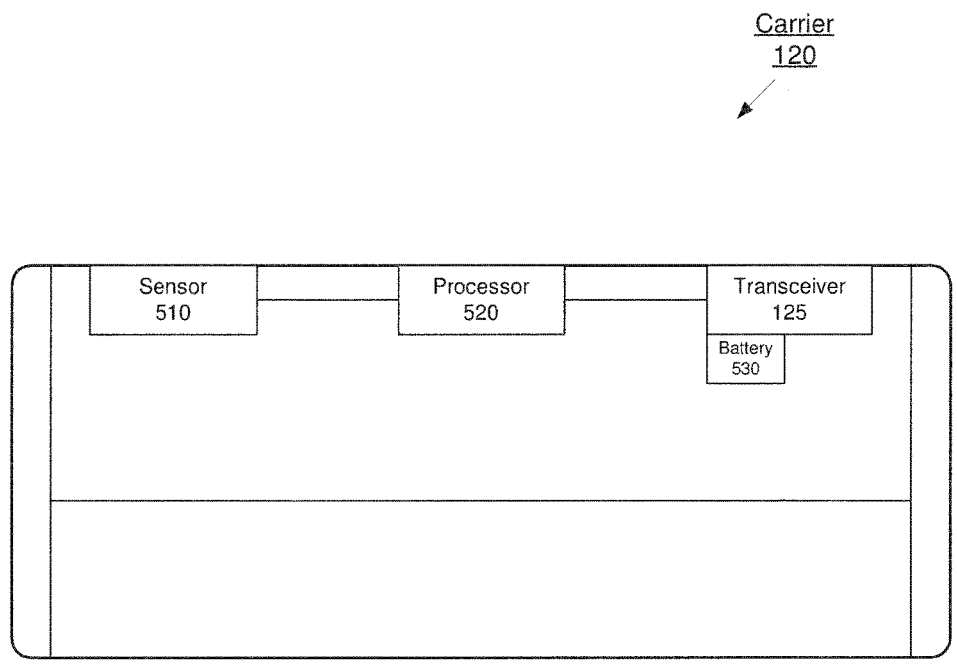
FIG. 5 shows a simplified schematic drawing of a carrier according to an exemplary embodiment of the present invention.

FIG. 5 shows a simplified schematic drawing of a carrier 120 according to an exemplary embodiment. The carrier 120 may be a component of pneumatic tube delivery system, such as the system 100 described above in FIG. 1. Furthermore, the exemplary carrier 120 includes a sensor 510, a processor 520 and a wireless communication transceiver 125. The sensor 510 may be disposed on any portion of the carrier 120 (e.g., on the interior, on the exterior, both, etc.) and may be able to detect and/or measure any number of characteristics relating to the carrier 120 and its contents. The information collected by the sensor 510 is sent to the processor 520 and the transceiver 125. For instance, the processor 520 analyzes information, such as measurable variables, collected by the sensor 510 and automatically takes appropriate action when certain conditions are met (e.g., an event has been detected, a threshold value has been exceeded, etc.). One exemplary action taken by the processor 520 will be to instruct the transceiver 125 to initiate wireless communication of the information, such as via the Bluetooth communication protocol. Specifically, the transceiver 125 transmits the collected information via wireless transmission to any receivers throughout the exemplary pneumatic tube delivery system. As noted above, the wireless receivers may be disposed on any number of components of the system, such as, but not limited to, workstations, blowers, diverters, transmission tubing, etc.

The information collected by the exemplary sensor 510 of the carrier 120 may include monitoring conditions such as temperature within the carrier 120. Accordingly, the sensor 510 may include a thermometer. If the temperature within the carrier 120 exceeds a predetermined threshold value, the processor 520 may include instructing the transmitter to notify the system via a warning and/or an alert. A system controller, such as the controller 110 of FIG. 1, may then take a predesignated action such as returning the carrier 120 to its sending station. Alternatively or in addition, the system controller 110 may provide a notification to the personnel (e.g., via email, text message, or other communication means such as a nurse call system.

According to a further embodiment, the sensor 510 of the carrier 120 may include a humidity sensor monitoring a level of humidity within the carrier 510. If a specific threshold value for the measured humidity is exceeded, an alert of a potential leak of the carrier contents and/or the delivery system (e.g., tubing) may be provided to the sending workstation, the destination workstation and the maintenance department.

Additional information may include forces applied to the carrier 120, wherein the sensor 510 features a G-force sensor. If a certain threshold is exceeded, the system may generate an alert to a maintenance department, as well as to the departments associated with the current transaction, as excessive force may lead to damage to the system, the carrier 120 and/or its contents (e.g., hemolysis). The sensor 510 may also include accelerometers to measure a speed of the carrier 120. Accordingly, if a typical speed (e.g., 22 fps) is not maintained by the carrier 120, an alert may be transmitted to the maintenance department. For instance, a blower that is not operating at optimal performance or a slight blockage within the tubing may hinder the delivery speed of the carrier 120. When the sensor 510 indicates that a speed of the carrier 120 is outside a desired speed range, the locations at which this occurs may be recorded to determine whether other carriers have had similar issues in the same location (i.e., there may be a problem with the tubing in the area where this problem has been sensed) and appropriate messages may be sent. The sensor 510 may also include a pressure sensor to detect a lack of pressure outside the carrier (i.e., within the tubing along the carrier path) that may affect the timing of the transaction. Once again, an alert may be transmitted to the maintenance department if the monitored pressure drops below a certain threshold value.

The exemplary sensor 510 may also monitor any number of carrier operation measurements, such as travel distance and time. Specifically, for a given transaction between a sending workstation and a receiving workstation, the sensor 510 may measure the distance traveled by the carrier 120 and the time of the transaction. The distance traveled for a specific transmission path may allow the system to identify the most efficient routes and delivery configurations for increased performance and reduced transaction times. If a time threshold for the transaction is exceeded, the carrier 120, where appropriate, warnings may be sent to interested parties and other designated actions may be taken such as automatically returning the carrier 120 to the sending workstation.

Furthermore, the sensor 510 may also monitor operation of the components of the carrier 120, such as a battery 530 associated with the transceiver 125. Accordingly, if a battery charge level for the transceiver 125 falls below a threshold value, the maintenance department or other personnel may be alerted to change the battery 530 and/or replace the carrier 120.

Additionally, the exemplary sensor 510 may also allow the system to monitor carrier inventory at each of the workstations. As opposed to manually counting and updating a current inventory of carriers at particular workstations, the system may automatically detect how many carriers are at a given workstation, and thus the operators of the system may be provided with a real-time carrier inventory as well as requests to forward empty carriers to designated locations. Alternatively, personnel may be directed to simply place a requested number of carriers 120 into the system with the controller 110 determining desired locations for each of the carriers 120 and automatically routing the carriers 120 to selected workstations to achieve a desired distribution of the empty carriers 120.

Figure 6:
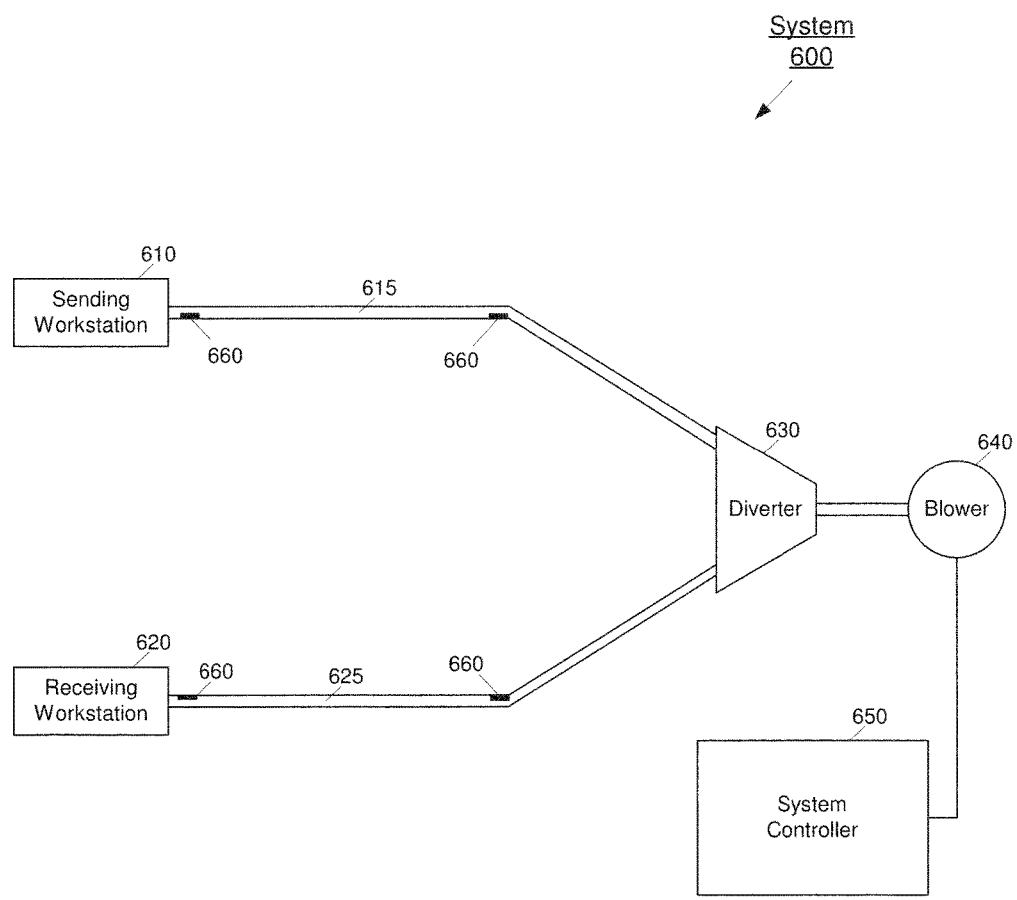
FIG. 6 shows a simplified schematic drawing of a pneumatic tube delivery system including sensors for monitoring the delivery of a carrier from a sending workstation to a receiving workstation according to an exemplary embodiment of the present invention.

FIG. 6 shows simplified schematic diagram of an exemplary pneumatic tube delivery system 600 including sensors 660 for monitoring the delivery of a carrier from a sending station 610 to a receiving station 620. As shown in FIG. 2, the pneumatic tube delivery system includes a diverter 630, a blower 640 and a system controller 650. Furthermore, the system 600 includes transmission tubing, such as tubing 615 connecting the sending station 610 to the diverter 630 and tubing 625 connecting the receiving station 620 to the diverter 630.

According to this embodiment, the sensors 660 may be disposed throughout any area of the delivery system, such as within the tubing 615 and 625. These exemplary sensors 660 are in communication with the system controller 650 and may detect any number of measurable conditions and operations, similar to the sensors 510 within the exemplary carriers 120. Specifically, the sensors 660 may measure conditions such as temperature, humidity and pressure within the transmission tubing 615, 625. The sensors 660 may further monitor the operations, such as a force applied to carriers 120 passing therethrough, a speed of carriers 120 passing therethrough, etc. Each of the monitored conditions and/or operations throughout the system 600 may be reported to the controller 650, with the controller 650 automatically taking appropriate action when predetermined threshold values for the measurements are exceeded.

A method of operation of the system will now be described with reference to the system depicted in FIG. 6, the carrier 120 depicted in FIG. 5 and the flow diagram of FIG. 7. The method 700 will be described in regard to the delivery of a carrier 120 from a sending workstation 610 to a receiving workstation 620. FIG. 7 shows an exemplary method 700 carried out by the system controller 650 implemented in accordance with an exemplary embodiment for illustrative general reference.

In a step 710, the system controller 650 receives delivery information from the sending workstation 610 requesting delivery of the carrier 120 to the specified receiving workstation 620. For instance, the sending workstation 610 may include an information reader with a user interface or any other device for gathering delivery information corresponding to the carrier 120 and its contents. In step 720, the system controller 650 determines a desired path from the sending workstation 610 to the receiving workstation 620 based on the delivery information and current system conditions. According to this exemplary embodiment, the path is from sending workstation 610 to the diverter 630 along tubing 615 and from the diverter 630 to the receiving workstation 620 along tubing 625.

In step 730, the system controller 650 establishes a communication link with the carrier 120 via the transceiver 125 while the carrier 120 travels along the path to the receiving workstation 620. As noted above, the communication link may be achieved using a short-ranged, low power protocol, such as the Bluetooth standard as would be understood by those skilled in the art.

In step 740, the system controller 650 receives via wireless radio communications carrier transit information pertaining to one of a delivery of the carrier along the path and a condition of the delivery system. For instance, as described above, the carrier transit information may include information such as, but not limited to, temperature measurements, humidity measurements, speed and distance measurements, time measurements, force and pressure measurements, etc.

In step 750, the system controller 650 adjusts operation of the components of the exemplary system 600 as required. For instance, the system controller 650 may automatically return the carrier 125 to the sending workstation 610 based on a detected condition (e.g., a detected leak or excessive temperature). In addition, the system controller 650 may select an alternate route for the carrier 125 to travel based on a problem detected within a portion of the delivery system (e.g., a leak or low pressure in one of the tubes) along the calculated route. In step 760, the system controller 650 may transmit an alert to any or all workstations of the system informing a user at either or both of the sending and workstations 610, 620 that the carrier 120 encountered a problem during delivery. Furthermore, the alert may inform the user of any adjustments may in the delivery of the carrier 120 (e.g., a re-routed destination, a returned of the carrier 120, etc.).

In addition to the functions discussed above for monitoring the delivery of the carrier 120 from the sending workstation to the receiving workstation, the exemplary embodiments may also utilize the speed and time measurements associated with the delivery to calculate any relative distance measurements, as well as to determine a position of a carrier within the system. Further features may also include the use of technology to determine any service and maintenance requirements throughout the systems, such as, but not limited to, air flow, pressure quality, worn or broken seals, damage to tubing, etc.

Those skilled in the art will understand that the above-described exemplary embodiments may be implemented in any number of manner, including as a separate software module, as a combination of hardware and software, etc. For example, the system controller 110 may be programs containing lines of code that, when compiled, may be executed on a processor.

Although these embodiments have been described in connection with specific forms and steps, it will be appreciated that various modifications other than those discussed above may be resorted to without departing from the spirit or scope of the invention as defined in the appended claims. For example, equivalent elements may be substituted for those specifically shown and described, certain features may be used independently of other features, and in certain cases, particular applications of elements may be reversed or interposed, all without departing from the spirit or scope of the invention.

What is claimed is:

1. A system for delivering items comprising:
   a network of tubing;
   a system controller controlling operation of the system;
   a plurality of carriers for delivering items, wherein a first one of the carriers includes a wireless transmitter and a sensor for sensing system data corresponding to a condition of the system;
   a plurality of workstations arranged throughout the system in communication with the network of tubing;
   at least one blower and at least one diverter, wherein the at least one blower is connected to at least two workstations of the plurality of workstations via the network of tubing passing through the at least one diverter; and
   a plurality of system transceivers arranged throughout the network of tubing and the plurality of workstations, wherein at least one of the system transceivers receives carrier transit information and system data from the wireless transmitter, and the system controller adjusts the operation of the system based on the carrier transit information and generates an indication of system conditions at a plurality of locations within the network of tubing based on the system data.

2. The system of claim 1, wherein the carrier transit information pertains to one of a delivery of the first carrier along a path.

3. The system of claim 1, wherein the system controller transmits an alert communication to at least one of the workstations based on one of the carrier transit information and the system conditions.

4. The system of claim 1, wherein the system data includes one of a temperature measurement, a humidity measurement, a speed measurement, a time measurement, a distance measurement, a force measurement, and a pressure measurement.

5. The system of claim 1, wherein at least one of the system transceivers communicates with the wireless transmitter of the first carrier via a short-range wireless communication link.

6. The system of claim 1, wherein the system controller determines carrier inventory information based on information received at the plurality of system transceivers.

7. A method for delivering items via carriers traveling through a pneumatic tube delivery system comprising:
   receiving delivery information for a first one of the carriers including information identifying a target receiving workstation to which the first carrier is to be sent;
   determining, based on the delivery information, a path for the first carrier from a sending work station to the receiving workstation;
   establishing a communication link with a sensor of the first carrier via a wireless transmitter of the first carrier while the carrier travels along the path to the receiving workstation;
   receiving via the communication link carrier transit information pertaining to a delivery of the carrier along the path and a system data corresponding to a condition of the delivery system;
   adjusting operation of the delivery system based on the carrier transit information; and
   generating an indication of system conditions at a plurality of locations within a network of tubing of the delivery system based on the system data.

8. The method of claim 7, further comprising:
   transmitting an alert communication to at least one of the sending workstation and the receiving workstation based on one of the carrier transit information and the system data.

9. The method of claim 7, wherein the system data includes one of a temperature measurement, a humidity measurement, a speed measurement, a time measurement, a distance measurement, a force measurement, and a pressure measurement.

10. The method of claim 7, wherein the communication link is a short-range wireless communication link.

11. The method of claim 7, wherein the delivery system includes a plurality of sensors collecting further carrier transit information pertaining to one of the delivery of the first carrier along the path and the condition of the delivery system, wherein at least one of the sensors sends the carrier transit information to a system controller.

12. The method of claim 7, wherein a system controller determines carrier inventory information based on information received from the system transceivers.

13. A non-transitory computer readable storage medium including a set of instructions, executable by a processor, for controlling the operations of a pneumatic tube delivery system, wherein the set of instructions, when executed by the processor, cause the processor to perform operations including:
   receiving delivery information from a sending workstation from which a carrier is to be sent to a receiving workstation, the delivery information identifying the receiving workstation;
   determining a path from the sending workstation to the receiving workstation based on the delivery information;
   establishing a communication link with a sensor of the carrier via a wireless transmitter of the carrier while the carrier travels along the path to the receiving workstation;

receiving via wireless radio communications carrier transit information pertaining to a delivery of the carrier along the path and a system data corresponding to a condition of the delivery system;

adjusting, by a system controller, operation of the system based on the carrier transit information; and generating an indication of system conditions at a plurality of locations within the network of tubing based on the system data.

14. The non-transitory computer readable storage medium of claim 13, wherein the system controller transmits an alert communication to at least one of the sending workstation and the receiving workstation based on one of the carrier transit information and the system conditions.

15. The non-transitory computer readable storage medium of claim 13, wherein the system data includes one of a temperature measurement, a humidity measurement, a speed measurement, a time measurement, a distance measurement, a force measurement, and a pressure measurement.

16. The non-transitory computer readable storage medium of claim 13, wherein at least one of the system transceivers communicates with the wireless transmitter of the carrier via a short-range wireless communication link.

17. The non-transitory computer readable storage medium of claim 13, wherein the delivery system includes a plurality of sensors collecting carrier transit information pertaining to one of a delivery of the carrier along the path and system data pertaining to a condition of the delivery system, wherein at least one of the sensors sends the carrier transit information to the system controller.

18. The non-transitory computer readable storage medium of claim 13, wherein the system controller determines carrier inventory information based on information received at the plurality of system transceivers.

19. A carrier for delivering items within a system, the carrier comprising:
- a housing including a storage component for storing content;
- at least one sensor collecting carrier transit information and system data, the carrier transit information pertaining to one of a delivery of the carrier along the path and the system data pertaining to a condition of the delivery system; and
- a wireless transmitter establishing a communication link between at least one system transceiver of the system and the sensor for transmitting the carrier transit information and the system data over the communication link while the carrier travels along a path from a sending workstation to a receiving workstation.

20. The carrier of claim 19, wherein the system data includes one of a temperature measurement, a humidity measurement, a speed measurement, a time measurement, a distance measurement, a force measurement, and a pressure measurement.

* * * * *